United States Patent [19]
Mamidi et al.

[11] Patent Number: 6,162,904
[45] Date of Patent: Dec. 19, 2000

[54] MANUFACTURING METHOD FOR INTRAVENEOUSLY ADMINISTRABLE IMMUNE GLOBULIN AND RESULTANT PRODUCT

[75] Inventors: Raja R. Mamidi, Pomona; Andranik Bagdasarian, San Dimas; Gorgonio Canaveral, Walnut, all of Calif.; Kazuo Takechi, Osaka, Japan

[73] Assignee: Alpha Therapeutic Corporation, Los Angeles, Calif.

[21] Appl. No.: 09/421,405

[22] Filed: Oct. 21, 1999

Related U.S. Application Data

[63] Continuation of application No. 08/997,952, Dec. 24, 1997, abandoned, which is a continuation of application No. 09/333,289, Jun. 15, 1999, abandoned.

[51] Int. Cl.[7] .............................. C07K 16/00; C12N 7/06; A61K 38/21
[52] U.S. Cl. .................. 530/390.1; 530/386; 530/387.1; 530/388.25; 530/389.1; 530/390.5; 530/402; 530/416; 530/418; 530/427; 424/85.5; 424/130.1; 435/236; 435/238; 435/239; 514/2; 514/8; 514/21
[58] Field of Search .............................. 530/390.1, 386, 530/387.1, 388.25, 389.1, 390.5, 402, 416, 418, 427; 424/85.5, 130.1; 435/236, 238, 239; 514/2, 8, 21

[56] References Cited

U.S. PATENT DOCUMENTS

| | | | |
|---|---|---|---|
| 5,110,910 | 5/1992 | Tsau | 530/390.1 |
| 5,132,406 | 7/1992 | Uemura et al. | 530/390.1 |
| 5,151,499 | 9/1992 | Kameyama et al. | 530/381 |
| 5,371,196 | 12/1994 | Yuki et al. | 530/390.1 |

*Primary Examiner*—Christopher S. F. Low
*Assistant Examiner*—Abdel A. Mohamed
*Attorney, Agent, or Firm*—Sughrue, Mion, Zinn, Macpeak & Seas, PLLC

[57] ABSTRACT

A process for producing an intravenously-administrable gamma globulin solution substantially free of contaminating viruses by heat treating for viral inactivation and fractionating an impure gamma globulin solution and then treating the purified gamma globulin with a solvent-detergent for further viral inactivation. In a continuous process disclosed herein, partially purified gamma globulin solids is not recovered as an intermediate product during the disclosed process. In the continuous process, the fractionation to obtain a purified gamma globulin solution is carried out without precipitation of the desired gamma globulin.

35 Claims, No Drawings

# MANUFACTURING METHOD FOR INTRAVENEOUSLY ADMINISTRABLE IMMUNE GLOBULIN AND RESULTANT PRODUCT

RELATIONSHIP TO OTHER APPLICATIONS

This is a combined continuation application of U.S. Ser. No. 08/997,952 filed Dec. 24, 1997 and of U.S. Ser. No. 09/333,289 filed Jun. 15, 1999, both now abandoned.

In this application common disclosure from each of the above applications is not duplicated. Where disclosure differs between the two parent patent applications, disclosure of parent U.S. Ser. No. 09/333,289, is stated to be related to a "continuous process", which terminology is used in U.S. Ser. No. 09/333,289, as describing "[t]he manufacturing method . . . in the sense that once the process is started with a quantity of impure starting fraction . . . the process runs through until its completion (providing highly purified gamma globulin as a resultant product) without the intermediate recovery of partially purified gamma globulin solids". On occasion, the term "non-continuous process" is used herein to refer to disclosure from parent U.S. Ser. No. 08/997,952 where such disclosure differs from, at times very similar disclosure, of parent U.S. Ser. No. 09/333,289.

BACKGROUND OF THE INVENTION

The present invention relates to an integral, multi-step commercial process for the production of intravenously administrable immune serum globulin containing IgG (γ-globulin) as the main ingredient.

Various processes are known for obtaining intravenously administrable γ-globulin solutions from starting materials resulting from Cohn fractionation of human plasma. Certain of the Cohn fractions contain higher titres of γ-globulin than others. Usual starting materials for a γ-globulin solution are Cohn Fraction II or Cohn Fraction II+III.

Although prior art processors employ various separation and sterilization techniques, process modifications are constantly sought for improving final product purity and safety, and overall yield.

Many commercial processes employ either a solvent/detergent step for viral inactivation, or a heat treatment step for viral inactivation. To date, the art has not provided a multi-step process beginning with Cohn Fraction II paste or II+III paste including two different viral inactivation procedures as part of an efficient, high yield γ-globulin manufacturing process. The manufacturing process can be continuous.

U.S. Pat. No. 5,151,499 by Kameyama et al. is directed to a process for producing viral inactivated protein compositions in which a protein composition is subjected to a viral inactivation for envelope viruses in a solvent/detergent treatment of the protein composition and a viral inactivation for non-envelope viruses in a heat treatment of the protein composition. The '499 patent teaches that preferably the solvent/detergent step occurs first and in the presence of a protease inhibitor, followed by a heat treatment. Where the heat treatment is carried out in the liquid state, the protein is first recovered from the solvent/detergent by adsorption onto an ionic exchange column, prior to any heat treatment. The liquid heat treatment can be carried out in the presence of a sugar, sugar alcohol or amino acid stabilizer. Although the '499 patent lists many starting protein compositions including immunoglobulin, its production examples employ Factor IX, thrombin, fibrinogen and fibronectin. Removal of denatured protein produced in a heat treatment step through fractionation is not considered.

U.S. Pat. No. 5,371,196 by Yuki et al. is directed to purifying secretory immunoglobulin A. A liquid heat treatment or various combinations of liquid heat treatment and solvent treatment inactivation are described. A polyethylene glycol fractionation is employed following each step and always as a final step. This patent does not relate to immune globulin of high γ-globulin titre.

Certain prior art processes for production of intravenously injectable γ-globulin solutions describe the incorporation of a liquid heat treatment carried out in the presence of sorbitol heat stabilizer in a multi-step purification procedure beginning with Cohn Fraction II+III paste. In U.S. Pat. No. 4,845,199 by Hirao et al., Cohn Fraction II+III is subjected to polyethylene glycol (hereinafter "PEG") fractionation (8% w/v PEG followed by 12% w/v PEG), then ion exchange chromatography (DEAE-Sephadex) and removal of human blood group antibody prior to a liquid heat treatment in the presence of sorbitol as a protein stabilizer. On the other hand, Example 1 of U.S. Pat. No. 4,876,088 by Hirao et al. describes the preparation of intravenously injectable γ-globulin solution from Cohn Fraction II+III paste in which the paste is suspended in water, its pH adjusted to 5.5 and centrifuged, with the supernatant then being heat treated for viral inactivation in the presence of 33% w/v of sorbitol, followed by PEG fractionation (6%/12%) which would remove heat denatured protein and then by other purification steps including DEAE-Sephadex ion exchange chromatography.

SUMMARY OF THE INVENTION

An object of the present invention is to provide an integral, commercially useable process for producing a highly purified γ-globulin solution from the Cohn fractionation process.

Another object of the present invention is to provide very pure intravenously administrable γ-globulin solution free of both envelope and non-envelope viruses, including all heat sensitive viruses.

A further object of the present invention is to provide a commercial γ-globulin process enabling removal of any denatured protein produced during heat sterilization prior to a second stage viral inactivation.

A further object of the present invention is to provide a continuous commercial γ-globulin production process without the need for intermediate recovery of γ-globulin protein through the carrying out, in order, of a heat sterilization, a PEG fractionation and a solvent detergent viral inactivation.

The above and other objects which will be apparent to the skilled artisan are provided by the present invention in which an alcoholic Cohn fraction, which may be partially purified, but is rich in γ-globulin, is heat treated in aqueous medium in the presence of a heat stabilizer for viral inactivation and is thereafter first subjected to PEG fractionation, and then to a second viral inactivation in the presence of a solvent, preferably a solvent-detergent mixture, for disruption of envelope viruses, followed by separation from the solvent or solvent-detergent mixture.

Also, the above and other objects which will be apparent to the skilled artisan are provided by the present invention in which an alcoholic Cohn fraction may be partially purified, but is rich in γ-globulin, is heat treated in aqueous medium in the presence of a heat stabilizer for viral inactivation, the heat treated solution is thereafter first subjected to PEG fractionation, and then without intermediate γ-globulin protein recovery to a second viral inactivation in the presence of a solvent, preferably a solvent-detergent mixture, for disruption of envelope viruses, followed by separation from the solvent or solvent-detergent mixture.

In one preferred embodiment of the continuous process of the present invention, bentonite is admixed with a collected PEG fractionation product for additional virus removal, prior to the solvent or solvent-detergent viral inactivation.

In a preferred embodiment of the present invention, sorbitol is the heat stabilizer and trialkyl phosphate is the solvent.

In another preferred embodiment of the present invention, denatured products of the heat treatment viral inactivation are removed by the PEG fractionation prior to the second viral inactivation for providing an exceedingly pure heat treated γ-globulin.

In another preferred embodiment of the present invention, any particulates present are removed prior to the solvent-detergent treatment.

In preferred embodiment of the continuous process of the present invention, the γ-globulin solution is treated with an anion exchange resin.

In preferred embodiments of the continuous process of the present invention, a single stage polyethylene glycol fractionation step is carried out without precipitation of the desired γ-globulin.

In yet another preferred embodiment of the continuous process of the present invention, the γ-globulin solution is treated with a cationic exchange resin, or by diafiltration and/or tangential flow filtration, following the completion of viral inactivation.

In still another embodiment of the invention, there is provided a heat-sterilized and solvent-detergent sterilized γ-globulin suitable for intravenous administration.

DETAILED DESCRIPTION OF THE INVENTION

The manufacturing method disclosed herein from U.S. Ser. No. 09/333,289 is a continuous process in the sense that once the process is started with a quantity of impure starting fraction containing immunoglobulin, such as Cohn Fraction II+III paste, the process runs through until its completion (providing highly purified gamma globulin as a resultant product) without the intermediate recovery of partially purified gamma globulin solids. Of note, during the polyethylene glycol fractionation stage of the continuous process disclosed herein, partially purified gamma globulin paste is not recovered as an intermediate product.

A fraction containing immunoglobulin is used as the starting material. This fraction is not particularly limited in so far as it originates from human plasma and contains an immunoglobulin fraction. Specific examples of such an immunoglobulin-containing fraction include Fraction II+III and Fraction II obtainable by ethanol fractionation of Cohn, and paste of immunoglobulin-containing fractions equivalent thereto. Other starting materials are Fractions I+II+III, and Fraction II+IIIw. Fraction III paste is usable in the continuous process. The starting material may contain impurities, such as human blood-group antibodies, plasminogen, plasmin, kallikrein, prekallikrein activator, IgM, IgA, IgG polymers (hereinafter "aggregates"), etc. A typical Fraction II & III starting material contains about 300 grams protein per kilogram paste.

In the non-continuous process, the preferred starting materials are Cohn Fraction II or Cohn Fraction II+III while in the continuous process they are Cohn Fraction II & III or Cohn Fraction II paste. When Cohn Fraction II+III paste is used in the non-continuous process, it is recommended that it first be subjected to a preliminary washing procedure to form Fraction II+IIIw, which is thereafter used in the non-continuous process of this invention. "Fraction II+IIIw" is a disodium phosphate solution-washed Cohn Fraction II+III precipitate. Also, Fraction II & IIIw can be used as a starting material in the continuous process.

Fraction II+IIIw can be obtained by suspending Fraction II+III precipitate in cold water for injection in a ratio of about 1 kilogram of II+III paste per about 20 volumes of water. A sodium phosphate solution is added to the final concentration of approximately 0.003 M sodium phosphate for solubilizing lipids, lipoproteins and albumin. Cold ethanol is added to bring the final alcohol concentration to about 20%. During the alcohol addition, temperature is gradually lowered to −5±1° C. and pH is maintained or adjusted to 7.2±0.1, for example by using acetate buffer or dilute sodium hydroxide. The Fraction II+IIIw precipitate which forms is recovered by centrifugation and/or filtration while maintaining the temperature at −5±1° C.

Prior to the first viral inactivation step of the present invention, various preliminary purification and/or aggregate-reducing steps can be carried out. For example, when Fraction II+IIIw paste is used, typically containing about 20% alcohol and more than 70% of the protein present as IgG, it can be suspended in 3 to 10 volumes, preferably 3 to 5 volumes for the discontinuous process, or in 3 to 20 volumes, preferably 10 to 15 volumes for the continuous process, of cold water at a temperature of about 0 to 5° C. and with pH being adjusted to be between 4.5 to 6.0, preferably 5.0 to 5.5 using pH 4.0 acetate buffer or hydrochloric acid. The mixture is agitated for about 2 to 15 hours to allow all of the γ-globulin to go into solution. Thereafter, undissolved protein such as albumin and α-globulins can be removed by centrifugation and/or filtration.

With Fraction II+III paste starting material used in the continuous process, each kilogram of Fraction II+III paste is suspended in 3 to 20 kg, preferably 13 to 17 kg, of cold water. The pH of the suspension is adjusted to 4.5 to 6.0, preferably 4.8 to 5.4. The suspension is mixed for 1 to 20 hours, preferably 2 to 10 hours, at 0 to 25° C., preferably 0 to 10° C. The insoluble material is then removed by filtration using depth filters or centrifugation. If filtration is used, about 1 to 5 w/w % filter aid may be added before separation. The centrifugate or the filtrate may be further clarified by a membrane filter. The clarified solution may be concentrated to about 1 to 12%, preferably 4 to 8%, protein by ultrafiltration using 10,000 to 100,000 molecular weight cut off (MWCO) membranes.

Where a different starting Cohn fraction is employed, the initial step or steps of the process can be appropriately selected where desired for carrying out a preliminary purification for obtaining a fraction of high IgG content to be further processed. For example, where Cohn Fraction II (contains over 95% IgG) has been separated from Cohn Fraction III, with Fraction II to be further processed, the initial processing can be at an acid pH of 3.2 to 5.0, preferably 3.8 to 4.2, as described by Uemura et al. U.S. Pat. No. 4,371,520, in order to break down immune globulin aggregates present into immune globulin monomers and dimers, since aggregates are known to possess anti-complementary activity (ACA). As another alternative, with Cohn Fraction II+III starting material, the Uemura, et al. patent low pH treatment can be carried out as an additional step following an initial purification step as above described and prior to the viral inactivating heat treatment step.

For the heat sterilization step in the discontinuous process, the immune globulin protein is dissolved in water or, if in the form of an aqueous mixture such as the filtrate collected from the above-described partial purification of Fraction II+III, it can be used as is, and a sugar, sugar alcohol and/or amino acid heat stabilizer is added thereto. The heat stabilizer is preferably sucrose, maltose, sorbitol or mannitol, most preferably sorbitol. The sugar or sugar alcohol is added to the immune globulin solution as a powder or first mixed with a small volume of water and then added, to provide a final concentration of about 10 to 50 w/v %, up to saturation. At this point, the aqueous solution of immune globulin contains sufficient water so that this solution contains about 1 to 6% total protein.

For the heat sterilization step, in the continuous process the immune globulin protein in the form of the aqueous mixture collected from the above-described partial purification, such as the filtrate from Fraction II+III paste purification, can be used as is or concentrated to about 1 to 12%, preferably 4 to 8%, protein by ultrafiltration, and a sugar, sugar alcohol and/or amino acid heat stabilizer is added thereto. The heat stabilizer is preferably sucrose, maltose, sorbitol or mannitol, most preferably sorbitol. The sugar or sugar alcohol is added to the immune globulin solution as a powder or first mixed with a small volume of water and then added, to provide a final concentration of about 25 to 50 w/w %, up to saturation, preferably 30 to 40 w/w %. At this point, the aqueous solution of immune globulin contains sufficient water so that this solution contains about 1 to 8% total protein.

Following addition of the heat stabilizer, in the discontinuous process the mixture is heated at about 50–70° C. for about 10–100 hours, preferably at about 60° C., for about 10 to 20 hours, for viral inactivation of heat sensitive viruses. Following addition of the heat stabilizer, in the continuous process the solution pH is adjusted to 4.5 to 6.5, preferably 5.0 to 6.0 and the mixture is heated at about 50–70° C. for about 1–20 hours, preferably for 10 to 11 hours at about 60° C., for viral inactivation of heat sensitive viruses. The heat treatment step not only inactivates viruses, but also through the protein denaturization effect thereof, can preferentially reduce the amount of certain undesirable proteins normally associated with Cohn Fractions II+III, such as prekallikrein, plasmin, plasminogen and IgA.

After the heat treatment, in the non-continuous process cold water to the extent necessary is added so that protein concentration is maintained at about 0.3 to 2.0%. The solution is cooled to 0–2° C.

After the heat treatment, in the continuous process the solution is either processed directly or diluted with cold water up to 5 times the volume of the heat treated solution. The solution is then cooled to 0–10° C., preferably 0 to 5° C.

Next, PEG fractionation is carried out on the heat treated solution. PEG fractionation is a well known procedure in the art of purification of immune globulin in order to separate the desired IgG monomer and dimer from IgG aggregate and from other impurities naturally occurring in the starting plasma protein fraction. However, in the instant process, the PEG fractionation also accomplishes a separation between the desired IgG monomer and dimer, and unwanted denatured protein products produced by the heat treatment. These denatured protein products are denatured prekallikrein activator, plasminogen, plasmin, IgA, IgM and aggregates.

PEG Fractionation in the Non-Continuous Process

Any of the PEG fractionation procedures documented in the prior art can be used. In general, two stages of PEG fractionation are carried out. In the first stage of PEG fractionation, PEG concentration and pH are selected so that the desired IgG monomer and dimer remain in solution while undesired proteins such as aggregate are precipitated out of solution. Following centrifugation and/or filtration, PEG concentration is increased with adjusting the pH to cause the desired IgG monomer and dimer to precipitate.

For example, a first stage of PEG fractionation can be carried out at a pH of about 5.0 to 7.5, preferably within about 6.5 to 7.5 pH when Fraction II+IIIw paste is used as starting material, and preferably within about 5.5 to 6.0 pH when Fraction II+III paste is used as starting material, with a PEG concentration ranging from about 4 to 8%, preferably either 4 to 6% when Fraction II+IIIw paste is used as starting material, or 6 to 8% when Fraction II+III paste is used as starting material. While maintaining cold temperatures of about 0–2° C., the first stage of PEG fractionation can be carried out for about 1 to 8 hours, after which the precipitate is removed as above-described. The filtrate will then have its pH adjusted to about 8.0 to 9.0, preferably about 8.5 to 8.9, and additional PEG added for final concentration of about 10 to 15%, preferably about 12%. The precipitate formed, which is purified immunoglobulin, is removed by filtration and/or centrifugation.

Further details of PEG fractionation procedures usable in the practice of the present invention can be found in the above-described U.S. Pat. No. 4,876,088 by Hirao et al. and U.S. Pat. No. 4,845,199 by Hirao et al.

PEG Fractionation in the Continuous Process

Any of the PEG fractionation procedures documented in the prior art can be used as long as PEG concentration and pH are selected so that the desired IgG monomer and dimer remain in solution while undesired proteins such as aggregate are precipitated out of solution. The PEG is added as a powder, flakes or as a 50% solution directly to the heat treated solution for providing the desired PEG concentration.

For example, the PEG fractionation can be carried out as described above for the first stage of PEG fractionation in the non-continuous process, that is, at a pH of about 5.0 to 7.5, preferably within about 6.0 to 7.5 pH when Fraction II+IIIw paste is used as starting material, and preferably within about 5.5 to 6.0 pH when Fraction II+III paste is used as starting material, with a PEG concentration ranging from about 4 to 8%, preferably either 4 to 6% when Fraction II+IIIw paste is used as starting material, or 6 to 8% when Fraction II+III paste is used as starting material. While maintaining cold temperatures of about 0–2° C., the PEG fractionation can be carried out for about 1 to 8 hours, after which the precipitate is removed by either centrifugation or filtration.

As an optional viral removal step in the continuous process, bentonite is added to the centrifugate or filtrate to a final concentration of about 0.05 to 2.0 w/w %, preferably 0.1 to 1.0 w/w %, and the mixture is mixed for 1 to 5 hours, and then the bentonite paste is removed by filtration.

The final essential step of the present invention is to carry out a second viral inactivation procedure utilizing a solvent or solvent-detergent mixture. As described below, further purification procedures, specifically those involving the use of ionic exchange resins, can be carried out prior to and/or following the solvent-detergent treatment.

In the non-continuous process, a particularly advantageous procedure is to carry out an anionic exchange treatment prior to the solvent detergent viral inactivation and then a cationic exchange treatment after the solvent detergent viral inactivation. By this procedure, certain undesirable protein materials (such as prekallikrein activator, IgA, IgM and albumin) found within human plasma can be removed from the IgG by use of the anionic exchanger and then further such materials (prekallikrein activator, IgA, IgM, albumin and PEG) along with the residual reagents used in the solvent-detergent treatment can be removed through the cationic exchange procedure. With the continuous process, the above-described anionic exchange treatment is one option prior to the solvent detergent viral inactivation, while in a preferred embodiment, the above-described cationic exchange treatment is carried out after the solvent detergent viral inactivation.

If not otherwise accomplished during the overall process the solution to be subjected to the solvent-detergent should be treated for removal of all particulate matter, which can include denatured protein. Therefore, it is preferred to filter the solution with a 1 micron or finer filter prior to solvent-detergent addition. This will also reduce the likelihood of virus being present within a large particle and thereby possibly avoiding exposure to the solvent-detergent.

In the continuous process, the filtrate may be diafiltered and/or concentrated up to about 12% protein, preferably 5–10% protein, and then subjected to the solvent, or solvent-detergent treatment.

Today, the preferred solvent for inactivation of envelope viruses is trialkyl phosphate. The trialkyl phosphate used in the present invention is not subject to particular limitation, but it is preferable to use tri(n-butyl)phosphate (hereinafter "TNBP"). Other usable trialkyl phosphates are the tri(ter-butyl)phosphate, the tri(n-hexyl)phosphate, the tri(2-ethylhexyl)phosphate, and so on. It is possible to use a mixture of 2 or more different trialkyl phosphates.

The trialkyl phosphate is used in an amount of between 0.01 to 10 (w/v) %, preferably about 0.1 to 3 (w/v) %.

The trialkyl phosphate may be used in the presence or absence of a detergent or surfactant. It is preferable to use trialkyl phosphate in combination with the detergent. The detergent functions to enhance the contact of the viruses in the immune globulin composition with the trialkyl phosphate.

Examples of the detergent include polyoxyethylene derivatives of a fatty acid, partial esters of anhydrous sorbitol such as Polysorbate 80 (Tradename: Tween 80, etc.) and Polysorbate 20 (Tradename: Tween 20, etc.); and non-ionic oil bath rinsing agent such as oxyethylated alkylphenol (Tradename: Triton X100, etc.) Examples include other surfactants and detergents such as Zwitter ionic detergents and so on.

When using the detergent, it is not added in a critical amount; for example, it may be used at concentrations between about 0.001% and about 10%, preferably between about 0.01% and 3%.

In the present invention, the trialkyl phosphate treatment of the immune globulin containing composition is carried out at about 20 to 35° C., preferably 25 to 30° C., for more than 1 hour, preferably about 5 to 8 hours (more preferably about 6 to 7 hours in the non-continuous process).

During the trialkyl phosphate treatment, immune globulin is present in the non-continuous process at about a 3 to 8% protein solution and in the continuous process at about a 5 to 10% protein solution, both in aqueous medium.

If not carried out prior to the solvent-detergent treatment, an anionic exchange treatment can be carried out on the solvent detergent treated immune globulin. Preferably, at least a cationic exchange treatment is carried out on the solvent-detergent treated product.

In the non-continuous process, the ionic exchange treatments are carried out with immune globulin dissolved in an aqueous solvent, generally having a pH of about 5–8, with where desired low ionic strength for maximum adsorption of IgG.

In the continuous process, the ionic exchange treatments are carried out on the immune globulin aqueous solution from solvent (or solvent detergent) processing, generally having a pH of about 4.5 to 6.5, with where desired low ionic strength for maximum adsorption of IgG.

The protein concentration for the ionic exchange treatment carried out after the solvent detergent treatment generally is within the range of about 1–15 w/v %, more preferably from about 3 to 10 w/v %. The ionic exchanger is equilibrated with the same aqueous solvent as used. Either a batch or continuous ionic exchange system can be carried out for the non-continuous process while the continuous system is used in the continuous process. For instance, anionic exchange batch-wise treatment can be carried out by mixing the immune globulin solution with the anionic exchanger in an amount from about 10 to 100 ml per ml of the pretreated anionic exchanger (for example, 1 gram of DEAE Sephadex A-50 resin swells to about 20 to 30 grams wet weight in 0.4% sodium chloride solution), stirring the mixture at about 0–5° C. for about 0.5 to 5 hours, and then filtering or centrifuging at 6,000 to 8,000 rpm for 10 to 30 minutes to recover the supernatant liquor. Continuous treatment can be affected by passing immune globulin solution through a column of the anionic exchanger at a rate from about 10 to 100 ml per ml of the ionic exchanger and recovering the non-adsorbed fraction.

The anionic exchanger to be used, for example, comprises anion exchanging groups bonded to an insoluble carrier. The anion exchanging groups include diethylaminoethyl (DEAE), a quaternary aminoethyl (QAE) group, etc., and the insoluble carrier includes agarose, cellulose, dextran, polyacrylamide, etc.

Usable cationic exchangers are carboxy methyl Sephadex (CM-Sephadex) CM-cellulose, SP-Sephadex, CM-Sepharose and S-Sepharose. For the non-continuous process, 1 ml of pretreated cationic exchanger (for example, 1 gram of CM-Sephadex C-50 resin swells to about 25–35 grams wet weight in 0.4% sodium chloride solution) is mixed with 0.5 ml to 5 ml of immune globulin solution and stirred at 0–5° C. for 1–6 hours. The suspension is centrifuged or filtered to recover the IgG adsorbed resin. Also, a continuous cationic exchange process can be employed in the non-continuous process as is employed in the continuous process.

With the continuous process for preparing purified immune globulin, pretreated cationic exchanger is used as a column bed through which the immune globulin solution from solvent (or solvent detergent) processing is passed in a continuous process at about 0–5° C.

When the above-described conditions are used with the cationic exchanger, the IgG will be adsorbed, and thereafter following washing of the protein-adsorbed cationic exchange resin, IgG can be eluted, for example by about a 1.4 N sodium chloride solution.

When ionic exchange treatments are not employed in the continuous process, the solvent (solvent detergent) treated solution is diafiltered and concentrated by tangential flow filtration for removal of solvent detergent and PEG. Where very low levels of solvent detergent and PEG are desired in the final product, a preferred processing is treatment with a cationic exchanger followed by tangential flow filtration.

Following the steps of the above process, the IgG is clarified, diafiltered and concentrated to the extent needed. If desired, a stabilizer such as D-sorbitol can be added and final adjustments made to yield a solution of a composition containing about 100 mg/ml IgG, and 50 mg/ml D-sorbitol, with pH being at 5.4. This solution is then sterile filtered through sterilized bacterial retentive filters and filled into vials.

As described with the continuous process of U.S. Ser. No. 09/333,289, the final IgG concentration can be about 50 to 100 mg/ml IgG and for additional removal of viruses, the IgG solution may be filtered through 35 nanometers or less porosity filters prior to use of the sterilized bacterial retentive filters.

The following examples are set forth to illustrate the invention but are non-limiting.

Where desired, in the discontinuous process other immune globulin purification procedures can be appropriately combined with the processes described herein. For example, a bentonite clarification step, useful for reducing the levels of kallikrein and pre-kallikrein activator can be employed. An illustration of this is set forth in Example 1, hereinbelow.

EXAMPLE 1

Heat Treated and Solvent-detergent Treated γ-Globulin

Six hundred and eighty five grams of Fr II+IIIw paste was suspended in about 11.9 kg of cold water. Sodium acetate trihydrate solution was added to the suspension to a final concentration of approximately 0.04M to selectively solubilize IgG. After mixing for about 15 minutes, pH of the suspension was adjusted to 4.8 with pH 4.0 acetate buffer. Cold alcohol (95%) was added to the suspension to a final concentration of 17%. During the alcohol addition the temperature of the suspension was lowered gradually to about −6° C. Three hundred and three grams of acid washed Celite 535 available from Celite Corporation was added as a filter aid to the suspension to a final concentration of about 2.0%. After mixing for one hour, the Celite and the Fraction III paste containing unwanted protein such as plasmin, plasminogen, IgA and IgM were then removed by filtration utilizing a filter press. The filtrate was further clarified by 0.45 μm and 0.2 μm filters.

The pH of the Fraction II+III w clarified solution was adjusted to 4.0 with 1.0 N hydrochloric acid and then concentrated by ultrafiltration to about 3.4 liters (⅕th the original volume). Cold water equal to the amount removed by the 1st ultrafiltration was added to the concentrated solution and it was again concentrated by ultrafiltration to about ⅕th the original volume. At this step, protein concentration of the solution was about 2%. The solution was further concentrated to about 4% and diafiltered against cold water until the conductivity of the solution was below 300 μS/cm to help avoid protein aggregation and denaturation during heat treatment. The solution was further concentrated to about 8.8% protein. D-sorbitol was added to the solution to a final concentration of about 33%. After mixing for 30 minutes, pH of the sorbitol containing solution was adjusted to 5.5 with 0.5 N sodium hydroxide. The solution was then heated for 10 hours at 60° C. After the heat treatment, cold water equal to 3 times the volume of the heat treated solution was added and the diluted solution was cooled to 0–2° C.

The pH of the solution was adjusted to 6.9 with 0.25 N sodium hydroxide and 50% polyethylene glycol (PEG) 3350 was added to the solution to give a final PEG concentration of 4%. Sodium chloride concentration of the solution was adjusted to about 8 mM to aid in precipitation of impurities and aggregates at pH 6.9. The precipitate so formed was removed by filtration. The pH of the filtrate was adjusted to 4.8 with 1.0 N hydrochloric acid and bentonite was added to a final concentration of about 0.25%. The pH of the bentonite suspension was readjusted to about 5.2 and then the suspension was filtered to remove bentonite. The filtrate pH was adjusted to 8.5 with 0.25 N sodium hydroxide and 50% PEG 3350 solution was added to a final PEG concentration of 12%. The precipitate so formed (purified immune globulin) was removed by centrifugation.

About 175 grams of purified immune globulin paste obtained as above was suspended in about 790 g of 0.3% sodium chloride solution. pH of the suspension was adjusted to 5.5 and then the suspension was mixed for 2½ hours. Sixty two grams of previously equilibrated DEAE-Sephadex A-50 resin (with 0.3% sodium chloride at pH 5.5), was added to the solution and the suspension was mixed for 2 hours. The suspension was then filtered to remove the resin. After adjusting the concentration of sodium chloride to 0.4%, tri-n-butyl phosphate (TNBP) and Polysorbate 80 mixture was added to the filtrate to yield a solution with final concentration of 0.3% TNBP and 1.0% Polysorbate 80. After overnight incubation, pH of the solution was adjusted to 5.8 and about 860 grams of previously equilibrated CM-Sephadex C-50 (with 0.4% sodium chloride at pH 5.8), was added. After mixing for 2 hours, the suspension was filtered. After washing the CM-Sephadex resin 3 times with 0.3% sodium chloride, adsorbed IgG was eluted with 1.4 N sodium chloride. The eluate was clarified, diafiltered and concentrated. D-sorbitol was added and final adjustments were made to yield a solution with composition of about 100 mg/mL IgG, 50 mg/mL D-sorbitol at pH 5.4. The solution was then sterile filtered through sterilized bacterial retentive filter and filled into vials.

The intermediate bentonite step in this Example is useful for further reducing the presence of hypotensive enzymes such as kallikrein and pre-kallikrein activator.

| Test Results on Product from Example 1 | |
|---|---|
| Test Parameters | |
| Anti-Complementary Activity ($CH_{50}$ u/mg IgG) | 0.34 |
| IgG Purity (%) | 100 |
| IgG Content (mg/mL) | 112.7 |
| Prekallikrein (% CBER Ref #3) | 21 |
| Measles Antibody (% CBER Ref Lot No. 176) | 0.67 |
| IgG Molecular Size Distribution by HPLC | |
| (%) Monomer | 82.2 |
| (%) Dimer | 17.4 |
| (%) Fragments | 0.10 |
| (%) Aggregates | 0.3 |
| Hepatitis A Antibody (titer) | 1:200 |
| Hepatitis B Antibody (titer) | 1:1024 |
| IgA (μg/mL) | 22 |
| IgM (μg/mL) | 16 |
| Plasminogen (ng/mL) | ND |

-continued

Test Results on Product from Example 1

| Test Parameters | |
|---|---|
| Plasmin (ng/mL) | 16 |
| pH | 5.4 |

ND = None Detected

EXAMPLE 2

Heat Treated and Solvent-Detergent Treated γ-Globulin

One (1) kg of Fr II+III paste was suspended in 4.5 kg of cold water at 0–2° C. After mixing for 1 hour, pH of the suspension was adjusted to 5.0 with 1 N hydrochloric acid. After mixing for 3 hours at pH 5.0, the precipitate was removed by centrifugation. D-sorbitol was added to the centrifugate to a final concentration of 33% and mixed for 1 hour. The pH of the suspension was adjusted to 5.5 and then it was heated for 10 hours at 60° C. After the heat treatment, cold water equal to 3 times the volume of the heat treated solution was added and the diluted solution was cooled to 0–2° C. Fifty percent polyethylene glycol (PEG) 3350 solution was added to a final concentration of 6% PEG. The pH of the 6% PEG suspension was adjusted to 5.7 with 0.5 N sodium hydroxide and the suspension was mixed for 2 hours. Acid wash Celite 535 was added to a final concentration of 1.5% and the suspension was mixed for 1 hour. The precipitate along with the Celite was removed by filtration. The pH of the filtrate was adjusted to 8.8 with 0.5 N sodium hydroxide, and the PEG concentration adjusted to 12% with the addition of 50% PEG solution. The pH of the 12% PEG suspension was readjusted to 8.8, the suspension being mixed for 1 hour and filtered to collect the purified immune globulin paste. About 251 g of purified immune globulin paste was recovered.

Two hundred fifty one grams of purified immune globulin paste obtained as above was suspended in about 1.4 kg of 0.3% sodium chloride solution. After mixing for 1 hour, pH of the suspension was adjusted to 6.0 with 5% acetic acid. After the paste was dissolved completely, 104 grams of DEAE-Sephadex A-50 resin, previously equilibrated with 0.3% sodium chloride at pH 6.0, was added to the solution and mixed for 2 hours. The resin was removed by filtration. The filtrate was further clarified through 0.2 µm filter. Concentration of sodium chloride in the clarified solution was increased to 0.4% by the addition of sodium chloride. Tri-n-butyl phosphate (TNBP) and Polysorbate 80 mixture was added to the solution to give a final concentration of 0.3% TNBP and 1.0% Polysorbate 80. The solution was then incubated for 1 hour at 27° C. and left overnight in a cold box at 4° C. Next day, pH of the solution was adjusted to 5.8 and 1.8 kg of CM-Sephadex C-50 resin previously equilibrated with 0.4% sodium chloride at pH 5.8, was added. After mixing for 2 hours, the resin was separated by filtration. After washing the CM-Sephadex resin 3 times with 0.3% sodium chloride, adsorbed IgG was eluted with 1.4 N sodium chloride. The eluate was clarified, diafiltered and concentrated. D-sorbitol was added and final adjustments were made to yield a solution with composition of about 100 mg/mL of IgG and about 50 mg/mL D-sorbitol. The solution was split into 2 parts, part A and part B. The pH of part A was adjusted to 5.4 and part B was adjusted to pH 4.3. The solutions of part A and part B were then individually sterile filtered through sterilized bacterial retentive filters and filled into vials.

Test Results on Product from Example 2

| Test Parameters | | |
|---|---|---|
| Anticomplementary Activity (CH$_{50}$ u/mg IgG) | <0.05 | |
| IgG Purity (%) | 100 | |
| IgG Content (mg/mL) | 104.2 | |
| Prekallikrein (% of CBER Ref #3) | ND | |
| Diphtheria Antibody (Antitoxin U/mL) | 8.2 | |
| IgG Molecular Size Distribution by HPLC | pH 5.4 | pH 4.3 |
| (%) Monomer | 88.8 | 97.5 |
| (%) Dimer | 10.9 | 2.3 |
| (%) Fragments | 0.3 | ND |
| (%) Aggregates | <0.3 | <0.3 |
| Hepatitis A Antibody (titer) | 1:100 | |
| IgA (µg/mL) | 78 | |
| IgM (µg/mL) | 28 | |
| Kallikrein (A$_{405}$) | 0.09 | |
| Plasminogen (ng/mL) | <8.4 | |
| Plasmin (ng/mL) | <8.4 | |

ND = None Detected

EXAMPLE 3

Manufacturing Method for Intravenous Immune Globulin and Resultant Product

One thousand eight hundred grams of Fr II+III paste was suspended in 15 kg of cold water. After mixing for one hour at 0 to 5° C., pH of the suspension was adjusted to about 5.0 with dilute acetic acid. After mixing the suspension for 3 hours, approximately 900 grams of filter aid (acid washed celite) was added and mixed for 45 minutes. The insoluble material along with the celite was removed by filtration. The filtrate was clarified and then concentrated by ultrafiltration, using 100,000 molecular weight cut off (MWCO) membranes, to an approximate protein concentration of 6%.

D-sorbitol was added to the concentrated protein solution to a final concentration of 33 w/w % and mixed at pH 5.0 until all the sorbitol was dissolved. The solution was then heated at 60° C. for 10 hours. The heated solution was cooled to less than 10° C. and diluted with equal weight of cold water. The pH of the diluted solution was adjusted to 5.7 with dilute sodium hydroxide solution and then a solution of 50% polyethylene glycol (PEG) 3350 was added to a final concentration of 6 w/w %. After mixing for approximately 2 hours at pH 5.7, the precipitate so formed was removed by filtration with acid washed celite filter aid added to 3% w/w. Approximately 3.5 kg of the 6% PEG filtrate was set aside for other experiments. After adjusting pH of the remaining 6% PEG filtrate to 4.9, bentonite was added in the amount of 1 g per kg of filtrate and the pH was allowed to go up to about 5.1. After mixing for 2 hours, the suspension was filtered to remove bentonite. The filtrate was then concentrated and diafiltered by ultrafiltration, using 100,000 MWCO membranes.

The pH of the solution was adjusted to about 6.5 with dilute sodium hydroxide and then about 0.4 kg pre-swollen DEAE Sephadex A-50 resin was added to the solution. After mixing the protein solution with resin, the resin was removed by filtration. A solvent detergent (SD) solution containing a mixture of tri-n-butyl phosphate (TNBP) and polysorbate 80 was added to the filtrate to a final concentration of 0.3 w/w % and 1.0 w/w %, respectively. After incubating the solution containing SD at 27° C. for 6 hours, the solution was cooled to 0 to 5° C., the conductivity was adjusted to approximately 7 mS/cm with sodium chloride solution and the pH was adjusted to 5.8. About 2.7 kg of pre-treated Cm Sephadex C-50 resin was added to the solution, mixed and then filtered to retain the resin. The resin containing the adsorbed IgG was washed with 0.3% sodium chloride solution and then the adsorbed IgG was eluted with 1.4M sodium chloride solution. The eluate was clarified, concentrated and diafiltered with cold water. D-sorbitol was added and final adjustments were made to yield a solution of a composition containing about 100 mg/ml IgG and 50 mg/ml D-sorbitol with pH being at about 5.4. After final adjustments, the solution was sterile filtered and filled into glass vials. Test results of the resultant product are presented in the following Table.

TABLE

Test Results of Example Product

| Test Parameter | Result |
| --- | --- |
| Protein (mg/ml) | 99.2 |
| IgG purity (%) | 100 |
| Molecular distribution: (by HPLC) | |
| Monomer (%) | 89 |
| Dimer (%) | 11 |
| Prekallikrein activator (% CBER Ref. Lot No. 3) | <2.5 |
| Anticomplementary activity ($CH_{50}$ U/mg IgG) | 0.2 |

Variations of the invention will be apparent to the skilled artisan.

What is claimed is:

1. A process for preparing an intravenously administrable gamma globulin solution which comprises:
   (a) heat treating an impure gamma globulin solution under time and temperature conditions sufficient for inactivating heat sensitive viruses;
   (b) subjecting the heat treated gamma globulin solution only once to polyethylene glycol fractionation for obtaining a purified gamma globulin solution wherein the polyethylene glycol fractionation is carried out in at least two stages in which impurities are removed as a precipitant in a first stage of polyethylene glycol fractionation and the gamma globulin is removed as a precipitant in a second stage of polyethylene glycol fractionation; and
   (c) treating the purified gamma globulin solution with an organic solvent for inactivating envelope viruses without a further polyethylene glycol fractionation.

2. The process of claim 1 wherein the impure gamma globulin solution is Cohn Fraction I+II+III, Cohn Fraction II+III, Cohn Fraction II+IIIw, or Cohn Fraction II.

3. The process of claim 1 wherein the impure gamma globulin solution is subjected to at least one step of purification prior to the heat treating step (a).

4. The process of claim 1 wherein the organic solvent further comprises a detergent.

5. The process of claim 1 wherein a bentonite clarification step is carried out after the first stage of polyethylene glycol fractionation.

6. An intravenously-administrable gamma globulin solution produced by the process of claim 1.

7. The process of claim 1 wherein the heat treating step (a) is carried out at about 50 to 70° C. for about 10 to 100 hours.

8. The process of claim 7 wherein the heat treating step (a) is carried out for about 10 hours at about 60° C.

9. The process of claim 1 wherein the organic solvent used in step (c) is an alkyl phosphate.

10. The process of claim 9 wherein the alkyl phosphate is tri-n-butyl phosphate.

11. The process of claim 10 wherein the organic solvent further comprises a detergent.

12. The process of claim 1 wherein after step (a) the gamma globulin solution is treated with an anionic exchange resin and with a cationic exchange resin.

13. The process of claim 12 wherein the anionic exchange resin treatment is prior to step (c) and the cationic exchange resin treatment is after step (c).

14. An intravenously-administrable gamma globulin solution produced by the process of claim 13.

15. A continuous process for preparing an intravenously administrable gamma globulin solution which comprises:
   (a) heat treating an impure gamma globulin solution under time and temperature conditions sufficient for inactivating heat sensitive viruses;
   (b) without recovery thereof, subjecting the heat treated gamma globulin solution to polyethylene glycol fractionation, without causing precipitation of the desired gamma globulin, for obtaining a purified gamma globulin solution; and
   (c) without recovery thereof, treating the purified gamma globulin solution with an organic solvent for inactivating envelope viruses.

16. The process of claim 15 wherein the impure gamma globulin solution comprises Cohn Fraction I+II+III, Cohn Fraction II+III paste, Cohn Fraction II+IIIw, or Cohn Fraction II.

17. The process of claim 15 wherein the impure gamma globulin solution comprises proteins from Cohn Fraction II+III paste.

18. The process of claim 15 wherein the impure gamma globulin solution is subjected to at least one step of purification prior to the heat treating step (a) and the partially purified solution is subjected to the heat treatment step (a) without its intermediate recovery.

19. The process of claim 15 wherein the organic solvent further comprises a detergent.

20. The process of claim 15 wherein after step (b) the gamma globulin solution is treated with an anionic exchange resin.

21. The process of claim 15 wherein after step (c), the gamma globulin solution without recovery thereof is concentrated by tangential flow filtration.

22. An intravenously-administrable gamma globulin solution produced by the process of claim 15.

23. The process of claim 15 wherein the heat treating step (a) is carried out at about 50 to 70° C. for about 10 to 20 hours.

24. The process of claim 23 wherein the heat treating step (a) is carried out for about 10 to 11 hours at about 60° C.

25. The process of claim 24 wherein the impure gamma globulin solution comprises proteins from Cohn Fraction II+III paste.

26. The process of claim 15 wherein the organic solvent used in step (c) is an alkyl phosphate.

27. The process of claim 26 wherein the alkyl phosphate is tri-n-butyl phosphate.

28. The process of claim 27 wherein the organic solvent further comprises a detergent.

29. The process of claim 15 wherein after step (c) the gamma globulin solution without recovery thereof is treated with a cationic exchange resin.

30. The process of claim 29 wherein after the cationic exchange treatment, the gamma globulin solution is concentrated by tangential flow filtration.

31. An intravenously-administrable gamma globulin solution produced by the process of claim 30.

32. The process of claim 15 wherein the polyethylene glycol fractionation is carried out only once and comprises at least one stage in which impurities are removed as a precipitant and the desired gamma globulin remains in solution.

33. The process of claim 32 wherein the organic solvent used in step (c) is an alkyl phosphate.

34. The process of claim 32 wherein a bentonite clarification step is carried out on the gamma globulin solution obtained after the polyethylene glycol fractionation.

35. The process of claim 34 wherein the bentonite treated solution is treated with an anionic exchange resin.

* * * * *